US00PP30232P2

(12) United States Plant Patent
Wood

(10) Patent No.: US PP30,232 P2
(45) Date of Patent: Feb. 26, 2019

(54) ***PHYSOCARPUS* PLANT NAMED 'SMNPMS'**

(50) Latin Name: *Physocarpus opulifolius*
Varietal Denomination: SMNPMS

(71) Applicant: Timothy D. Wood, Spring Lake, MI (US)

(72) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/732,303

(22) Filed: Oct. 20, 2017

(51) Int. Cl.
*A01H 5/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Physocarpus* plant named 'SMNPMS', characterized by its relatively compact, upright and uniform plant habit; vigorous growth habit; freely branching habit; dark greyed purple-colored leaves; and good garden performance.

2 Drawing Sheets

Botanical designation: *Physocarpus opulifolius*.
Cultivar denomination: 'SMNPMS'.

BACKGROUND OF THE INVENTION

The present invention relates to a new and distinct *Physocarpus* plant, botanically known as *Physocarpus opulifolius* and hereinafter referred to by the name 'SMNPMS'.

The new *Physocarpus* plant is a product of a controlled breeding program conducted by the Inventor in Grand Haven, Mich. The objective of the breeding program is to create new compact *Physocarpus* plants with attractive leaf coloration and mildew resistance.

The new *Physocarpus* plant originated from an open-pollination in 2008 in Grand Haven, Mich. of *Physocarpus opulifolius* 'Seward', disclosed in U.S. Plant Pat. No. 14,821, as the female, or seed, parent with an unknown selection of *Physocarpus opulifolius* as the male, or pollen, parent. The new *Physocarpus* plant was discovered and selected by the Inventor in 2012 as a single plant within the progeny of the stated open-pollination in a controlled environment in Grand Haven, Mich.

Asexual reproduction of the new *Physocarpus* plant by softwood stem cuttings in a controlled environment in Grand Haven, Mich. since 2012 has shown that the unique features of this new *Physocarpus* plant are stable and reproduced true to type in successive generations of asexual reproduction.

SUMMARY OF THE INVENTION

Plants of the new *Physocarpus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNPMS'. These characteristics in combination distinguish 'SMNPMS' as a new and distinct *Physocarpus* plant:

1. Relatively compact, upright and uniform plant habit.
2. Vigorous growth habit.
3. Freely branching habit.
4. Dark greyed purple-colored leaves.
5. Good garden performance.

Plants of the new *Physocarpus* can be compared to plants of the female parent, 'Seward'. Plants of the new *Physocarpus* differ from plants of 'Seward' in the following characteristics:

1. Plants of the new *Physocarpus* are more compact than plants of 'Seward'.
2. Plants of the new *Physocarpus* are more upright than and not as outwardly spreading as plants of 'Seward'.

Plants of the new *Physocarpus* can be compared to plants of the *Physocarpus opulifolius* 'SMPOTW', disclosed in U.S. Plant Pat. No. 26,749. In side-by-side comparisons, plants of the new *Physocarpus* differ from plants of 'SMPOTW' in the following characteristics:

1. Plants of the new *Physocarpus* are more upright than and not as outwardly spreading as plants of 'SMPOTW'.
2. Plants of the new *Physocarpus* have larger leaves than plants of 'SMPOTW'.
3. Plants of the new *Physocarpus* have darker greyed purple-colored leaves than plants of 'SMPOTW'.

BRIEF DESCRIPTION OF THE PHOTOGRAPHS

The accompanying colored photographs illustrate the overall appearance of the new *Physocarpus* showing the colors as true as it is reasonably possible to obtain in colored reproductions of this type. Colors in the photographs may differ slightly from the color values cited in the detailed botanical description which accurately describe the colors of the new *Physocarpus*.

The photograph on the first sheet is a side perspective view of a typical plant of 'SMNPMS' grown in an outdoor nursery.

The photograph on the second sheet is a side perspective view of a typical plant of 'SMNPMS' grown in a container.

DETAILED BOTANICAL DESCRIPTION

The aforementioned photographs and following observations, measurements and values describe plants grown during the spring and summer in ground beds in an outdoor nursery and in three-gallon containers in a polyethylene-covered greenhouse in Grand Haven, Mich. and under cultural practices typical of commercial *Physocarpus* production. During the production of the plants, day temperatures ranged from 18° C. to 25° C. and night temperatures ranged from ranged from 5° C. to 10° C. Plants were two years old when the photographs and the description were taken. In the description, color references are made to The Royal Horticultural Society Colour Chart, 2015 Edition, except where general terms of ordinary dictionary significance are used.

Botanical classification: *Physocarpus opulifolius* 'SMNPMS'.

Parentage:

*Female, or seed, parent.*—*Physocarpus opulifolius* 'Seward', disclosed in U.S. Plant Pat. No. 14,821.

*Male, or pollen, parent.*—Unknown selection of *Physocarpus opulifolius*, not patented.

Propagation:

*Type.*—By softwood stem cuttings.

*Time to initiate roots, summer.*—About 25 days at temperatures about 24° C.

*Time to produce a rooted young plant, summer.*—About two months at temperatures about 24° C.

*Root description.*—Medium in thickness; fibrous and fleshy; typically white and brown in color, actual color of the roots is dependent on substrate composition, water quality, fertilizer, substrate temperature and physiological age of roots.

*Rooting habit.*—Freely branching; medium density to dense.

Plant description:

*Plant and growth habit.*—Perennial shrub; relatively compact, upright and uniform plant habit; vigorous growth habit.

*Branching habit.*—Freely branching habit with about 15 lateral branches developing per plant; pinching enhances lateral branch development.

*Plant height.*—About 48 cm.

*Plant diameter* (*area of spread*).—About 65 cm.

Lateral branch description:

*Length.*—About 30 cm to 60 cm.

*Diameter.*—About 4 mm.

*Internode length.*—About 2 cm.

*Texture.*—Smooth, glabrous.

*Aspect.*—Erect to outwardly.

*Color.*—Close to 59B.

Leaf description:

*Arrangement.*—Alternate, simple.

*Length.*—About 5 cm.

*Width.*—About 4 cm.

*Shape.*—Roughly rhomboid, tri-lobed.

*Apex.*—Acute.

*Base.*—Cordate.

*Margin.*—Doubly serrate.

*Texture, upper and lower surfaces.*—Rugose, glabrous.

*Venation pattern.*—Palmate.

*Color.*—Developing leaves, upper surface: Close to N92A. Developing leaves, lower surface: Close to 188A. Fully expanded leaves, upper surface: Close to N186A; venation, close to 156A. Fully expanded leaves, lower surface: Close to 191A; venation, close to 156A.

*Petioles.*—Length: About 1.7 cm. Diameter: About 2 mm. Texture, upper and lower surfaces: Smooth, glabrous. Color, upper surface: Close to 183B. Color, lower surface: Close to 182B.

Flower description: Flower initiation and development has not been observed on plants of the new *Physocarpus* to date.

Garden performance: Plants of the new *Physocarpus* have been observed to have good garden performance and to tolerate rain, wind and temperatures ranging from about −32° C. to about 36° C.

Pathogen & pest resistance: Plants of the new *Physocarpus* have not been shown to be resistant to pathogens and pests common to *Physocarpus* plants.

It is claimed:

1. A new and distinct *Physocarpus* plant named 'SMNPMS' as illustrated and described.

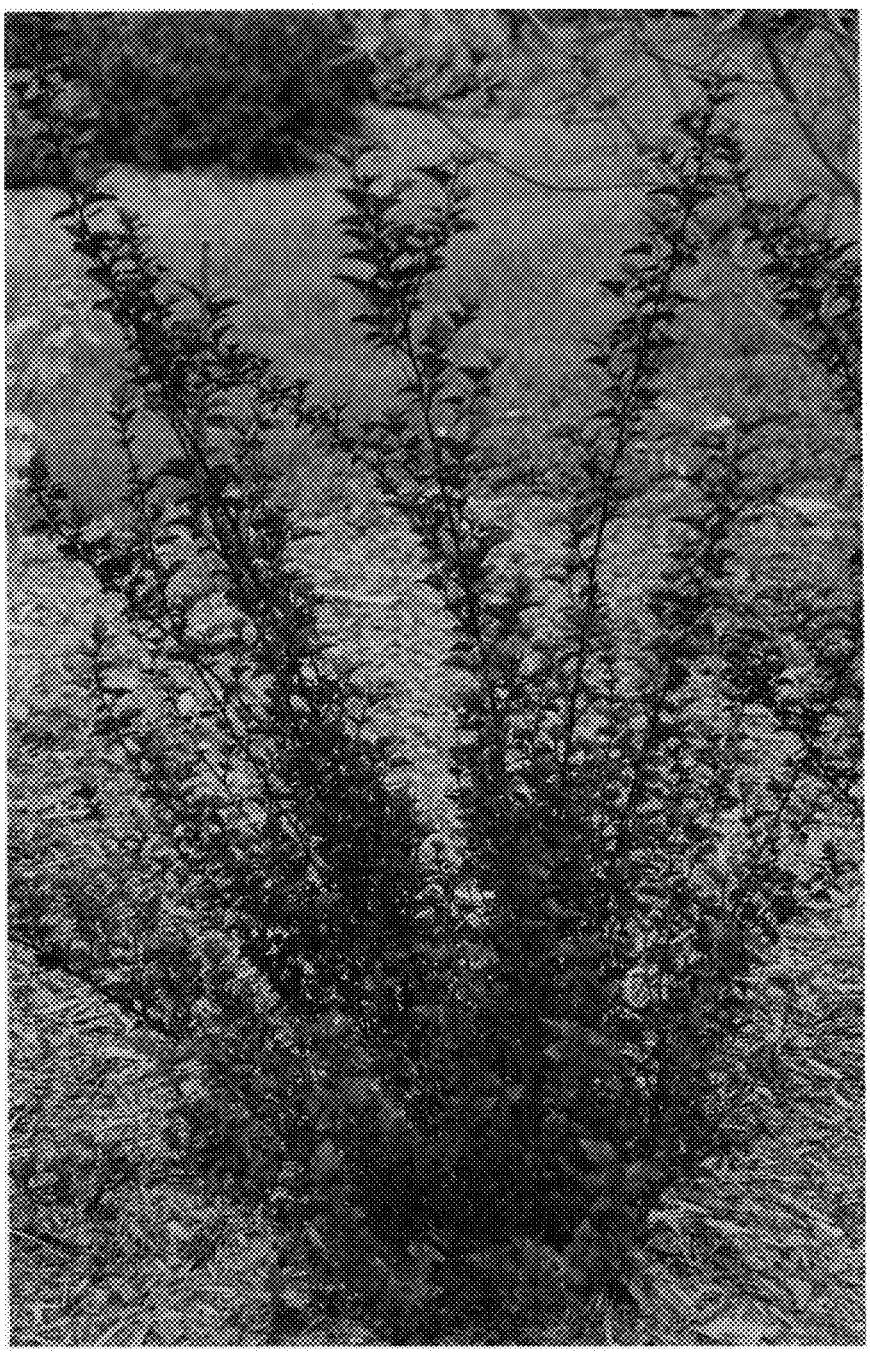

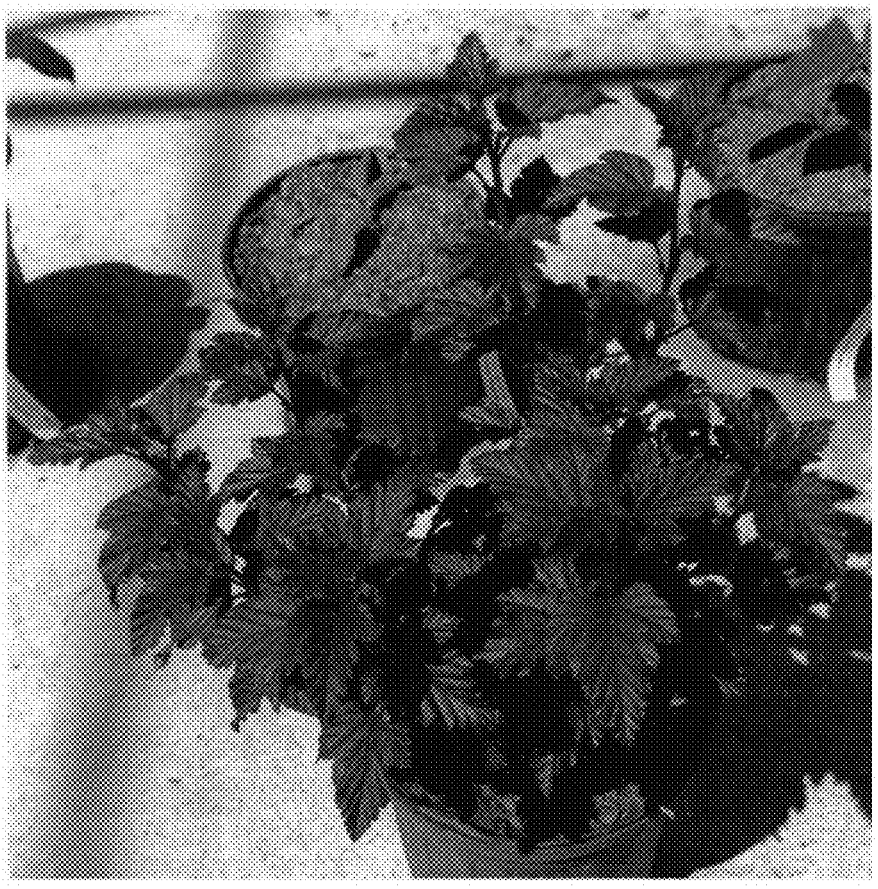

* * * * *